United States Patent [19]

Bayer et al.

[11] Patent Number: 5,013,655
[45] Date of Patent: May 7, 1991

[54] PROCESS FOR THE PREPARATION OF COLORANTS OR MONACOLIN K IN A STERILE FLUIDIZED BED OF LOW WATER CONTENT

[75] Inventors: Thomas Bayer, Hanover; Rainer Buchholz, Unnau; Hans-Matthias Deger, Hofheim am Taunus; Joachim Wink, Offenbach, all of Fed. Rep. of Germany

[73] Assignee: Hoechst Aktiengesellschaft, Frankfurt am Main, Fed. Rep. of Germany

[21] Appl. No.: 492,796

[22] Filed: Mar. 13, 1990

Related U.S. Application Data

[63] Continuation of Ser. No. 298,708, Jan. 19, 1989.

[30] Foreign Application Priority Data

Jan. 21, 1988 [DE] Fed. Rep. of Germany ....... 3801588

[51] Int. Cl.$^5$ .................... A61K 31/365; C12P 1/02; C12N 11/00; A23L 1/27
[52] U.S. Cl. ................................. 435/119; 435/125; 435/171; 435/911
[58] Field of Search ................ 435/119, 125, 171, 911

[56] References Cited

U.S. PATENT DOCUMENTS

| | | | |
|---|---|---|---|
| 3,765,906 | 10/1973 | Yamaguchi et al. | 99/148 |
| 3,993,789 | 11/1976 | Moll et al. | 426/250 |
| 4,031,250 | 6/1977 | Haas et al. | 426/18 |
| 4,046,921 | 9/1977 | Akao et al. | 435/255 |
| 4,145,254 | 3/1979 | Shepherd et al. | 195/81 |
| 4,323,648 | 4/1982 | Tanzawa et al. | 435/125 |
| 4,442,209 | 4/1984 | Miyake et al. | 435/119 |
| 4,560,479 | 12/1985 | Heijnen | 435/167 |
| 4,746,615 | 5/1988 | Buchholz et al. | 435/311 |

FOREIGN PATENT DOCUMENTS

| | | |
|---|---|---|
| 0106146 | 4/1984 | European Pat. Off. |
| 2724992 | 12/1977 | Fed. Rep. of Germany |
| 2461642 | 5/1978 | Fed. Rep. of Germany |
| 3006215 | 11/1980 | Fed. Rep. of Germany |
| 3625698 | 2/1988 | Fed. Rep. of Germany |
| 2505856 | 11/1982 | France |

OTHER PUBLICATIONS

European Search Report for European Patent Application EP 89 10 0294.
M. Yoshimura et al., Agr. Biol. Chem., vol. 39, No. 9, pp. 1789-1795 (1975).
T. Hiroi et al., Chem. Abstracts, vol. 83, Nr. 7183j (1975).
List of Cultures 1983, Centraalbureau Voor Schimmelcultures, p. 187.

*Primary Examiner*—Herbert J. Lilling
*Attorney, Agent, or Firm*—Finnegan, Henderson, Farabow, Garrett, and Dunner

[57] ABSTRACT

The invention relates to a process for the preparation of colorants and/or active compounds by culturing a microorganism of the genus Monascus in a sterilizable fluidized-bed fermenter of low water content, such as was proposed in German Patent Application P 3,625,698.6. The fluidizable particle used here is the microorganism itself—in pellet form or grown on carriers—which can be supplied with nutrients by spraying in substrate solutions. The colorants and/or active compounds are isolated by extraction with organic solvents.

5 Claims, No Drawings

PROCESS FOR THE PREPARATION OF COLORANTS OR MONACOLIN K IN A STERILE FLUIDIZED BED OF LOW WATER CONTENT

This is a continuation of application Ser. No. 07/298,708, filed Jan. 19, 1989.

The invention relates to a process for the preparation of colorants and/or active compounds by culturing a microorganism of the genus Monascus in a sterile fluidized bed of low water content. The culturing of the microorganisms is carried out in a sterilizable fluidized-bed fermenter such as was proposed in German Patent Application P 3,625,698.6.

The manifold possible applications of reactions in a fluidized-bed fermenter are shown in European Patent Application 106,146, wherein a large number of different microbial metabolites and enzymes were prepared biologically by fermentative conversion of precursors or by addition of effectors. In this process, the microorganisms are converted into fluidizable granules. The precursors or effectors are either incorporated beforehand into the granules or are sprayed as a solution or suspension onto the granules in the fluidized-bed fermenter. Using such a process, substances can be prepared in acceptable yields, which are accessible by chemical-synthetic methods only with difficulty or not at all.

The fermentative preparation of pharmacologically active compounds with the use of microorganisms of the genus Monascus has been disclosed, for example, in German Offenlegungsschrift 3,006,215. In the latter, the preparation of monacolin K, which is an antihypercholesterinemic substance, is described.

The preparation and use of pigments which have been obtained by culturing of microorganisms of the genus Monascus is the subject of a number of patents (U.S. Pat. Nos. 4,031,250; 3,765,906; DE-B 2,724,992; DE-B 2,461,642; FR-B 2,505,856).

Microorganisms of the genus Monascus have been used for a long time in South East Asia for the production of red dyes for the coloring of foodstuffs. The culturing is carried out on rice, fermentation material being mixed at certain intervals.

Because of this simple technique, the fungi can be only inadequately supplied with oxygen. A risk of contamination by extraneous organisms also cannot be excluded from this non-sterile process.

The biomass can be worked up by extraction. Numerous organic solvents, such as methanol, ethanol, acetone or ethyl acetate, are suitable for extracting the dyes which are sparingly soluble in water.

The total dried biomass is also used as a red foodstuffs additive in Asia.

Processes are also known for rendering the dyes more soluble in water. For this purpose, the pigments are reacted with the most diverse nitrogen-containing organic compounds such as, for example, amino acids, proteins or nucleic acids.

Most recently, submerse processes have also been developed as has been stated, for example, in German Patent 2,724,992. Disadvantages of submerse processes are the extensive dilution of the products formed and the often large quantities of water which make working-up expensive. Moreover, it is desirable to use a process which approaches the natural surface processes. This condition is met by the fluidized-bed process which, furthermore, can be carried out under sterile conditions (German Patent Application P 3,625,698.6), so that a risk of contamination by other microorganisms or their metabolic products which may be toxic is prevented. This is important in particular for pharmaceuticals and for the use of colorants in the foodstuffs sector.

The invention now relates to:

A process for the preparation of colorants and/or active compounds, wherein a microorganism of the genus Monascus is cultured in a sterile fluidized bed of low water content until the colorant and/or the active compound accumulates in the culture, and wherein, if appropriate, the colorant and/or the active compound is then isolated.

Active compounds are understood to be biologically active substances, in particular pharmaceuticals such as monacolin K. Examples of microorganisms of the genus Monascus, which can be used, are:

*Monascus albidus*, M. albus, M. anka, M. araneous, M. bisporus, M. kaoliang, M. major, M. paxii, M. pilosus, M. pubigerus, M. ruber, M. purpureus, M. rubiginosus, M. rubropunctutus, M. serorubescens, M. vitreus or mutants or variants thereof. The following are particularly suitable: *M. purpureus* CBS 10907, *M. ruber* CBS 34650 and *M. ruber* CBS 13560. Mutants or variants are produced in a manner known per se by physical means, for example by irradiation with ultraviolet or X-rays or by chemical mutagens such as ethyl methanesulfonate (EMS) or 2-hydroxy-4-methoxybenzophenone (MOB).

A sterilizable fluidized-bed fermenter, such as has been proposed in German Patent Application P 3,625,698.6, which is incorporated herein by reference, is suitable for carrying out the process.

Before the start of the fermentation, the fermenter is sterilized, for example by introducing superheated steam. The fluidized-bed fermenter prepared in this way is then not filled, for instance, by the finished biomass of the microorganism bred in another fermenter, which would with certainty lead to contamination with extraneous organisms, but the fluidized-bed fermenter is charged only with a submerse inoculation culture, bred in a smaller fermenter, under the usually applied sterile conditions. The microorganism can be propagated, for example, by two different processes. In submerse bubble-column operation in a liquid nutrient medium, pellets are bred which can be propagated as fluidizable particles without carriers. In the other case, a solid carrier, for example rice, millet or other cereal species or even sintered glass is used for letting the microorganisms grow on them, it being possible for the carrier materials to be at the same time also the substrate. In this case, the microorganisms are located in the fluidized bed even during the growth phase. As soon as a sufficient quantity of microorganisms has formed in the bubble-column operation, the spent substrate solution is removed by means of filter elements which are installed in the vicinity of the bottom of the fermenter. This procedure ensures that the fluidized-bed fermenter then contains a culture of a microorganism, which culture is uncontaminated by extraneous organisms. To carry out the actual fluidized-bed reaction, the mass of microorganisms, which has been freed from the spent culture broth until a pasty consistency is reached, is fluidized from below by introducing a gas stream. For this purpose, compressed air or oxygen is used which has beforehand been forced through sterile filters, so that no extraneous microorganisms can be introduced by the gas stream into the fluidized-bed reactor.

The gas used for fluidizing the biological material can be circulated. In case, the gas stream is passed into a thermosatically controllable air humidifier and the gas, cooled and saturated with moisture, is reintroduced into the fermenter. Alternatively, the gas stream can also be passed straight through.

The nutrient solution required for growth during the fluidized-bed fermentation is provided in a stock vessel and sprayed into the reactor in the form of finely dispersed droplets, unless the microorganisms utilize the carrier, which contains nutrients and on which they have grown, as the exclusive source of nutrients.

Particular care must be taken to ensure that the microorganisms do not dry out. This purpose is served by the thermostatically controllable air humidifier which ensures that the gas stream being passed in is saturated with moisture. Furthermore, sterile water can be fed into the fermenter at any time, if necessary, and the microorganisms can thus be moistened.

During the fermentation, the $CO_2$ content of the circulating gas increases steadily and the oxygen content decreases correspondingly. However, a constant gas composition is a prerequisite for optimum fermentation. For this reason, the fluidized-bed fermenter is fitted with control elements which control the continuous removal of the carbon dioxide. The quantities of gas purged are replaced by a feed of oxygen or air via an opening in the lower part.

The pigments and/or active compounds can —if required be—readily isolated by known processes from the cell mass obtained, for example by extraction with a suitable solvent such as hexane, methanol, ethanol, acetone or ethyl acetate. This extraction can also be carried out in the fermenter, with or without previous drying of the biomass.

The process according to the invention is described in detail in the examples that follow.

EXAMPLE 1

The *Monascus purpureus* CBS 10907 strain is bred in a small fermenter of 15 liter capacity in 2-3 days to give an inoculation culture. The medium contains 10 g/l of rice. Breeding is carried out at 30° C., with air being passed in (7.5 l/minute) and with a stirrer speed of 500 rpm.

This preculture is used for inoculating the fluidized-bed fermenter according to German Patent Application P 3,625,698.6, which has previously been filled with 25 kg of rice, humidified and sterilized with steam at 121° C. for 30 minutes.

At an operating temperature of 30° C., 60 kg of moist mass are obtained after a culturing period of 7 days. The pigments can be extracted with acetone from this mass.

EXAMPLE 2

The *Monascus ruber* CBS 34650 strain is bred in the fluidized-bed reactor on a synthetic medium in such a way that pellets are produced. After the nutrients have been consumed, the substrate solution is drained via filter elements and the pellets are fluidized. The supply of nutrients in the fluidized bed is carried out by spraying with a sterile nutrient solution. The fermentation is terminated after 6 days. The pigments are separated from the biomass by extraction with acetone.

We claim:

1. A process for the preparation of colorants or monocolin K, wherein a microorganism of the genus Monascus is cultured in a sterile fluidized bed of low water content until the colorant or the monacolin K accumulates in the culture and, the colorant or the monacolin K is then isolated.

2. The process as claimed in claim 1, wherein a microorganism selected from the group consisting of: *Monascus albidus, M. albus, M. anka, M. araneous, M bisporus, M. kaoliang, M. major, M. paxii, M. pilosus, M. pubigerus, M. ruber, M. purpureus, M rubiginosus, M. rubropunctatus, M. serorubescens, M. vitreus* or mutants or variants thereof is used.

3. The process as claimed in claim 1, wherein the microorganisms *M. purpureus* CBS 10907, *M. ruber* CBS 34650 or *M. ruber* CBS 13560 on solid carriers are used.

4. The process as claimed in claim 1, wherein the microorganisms are cultured in the form of pellets without solid carriers.

5. The process as claimed in claim 1, wherein the extraction of the colorants or monoacolin takes place in the fluidized-bed reactor.

* * * * *

UNITED STATES PATENT AND TRADEMARK OFFICE
CERTIFICATE OF CORRECTION

PATENT NO. : 5,013,655
DATED : May 07, 1991
INVENTOR(S) : Thomas Bayer et al.

It is certified that error appears in the above-identified patent and that said Letters Patent is hereby corrected as shown below:

On the Title page

Item [75] Inventors, after "Bayer", the word "Hanover" should read --Hannover--.

Claim 1, column 4, line 24, "monocolin" should read --monacolin--.

Claim 1, column 4, line 27, after "and" delete ",".

Claim 2, column 4, line 31, "*M*" (fourth occurrence) should read --*M.*--.

Claim 2, column 4, line 33, "*M*" (third occurrence) should read --M.--.

UNITED STATES PATENT AND TRADEMARK OFFICE
CERTIFICATE OF CORRECTION

PATENT NO. : 5,013,655

DATED : May 7, 1991

INVENTOR(S) : Thomas Bayer, et. al.

It is certified that error appears in the above-identified patent and that said Letters Patent is hereby corrected as shown below:

Claim 5, column 4, line 44, "monoacolin" should read --monacolin K--.

Signed and Sealed this

Twenty-third Day of February, 1993

*Attest:*

STEPHEN G. KUNIN

*Attesting Officer*    *Acting Commissioner of Patents and Trademarks*